United States Patent [19]

Bull et al.

[11] Patent Number: 5,418,227
[45] Date of Patent: May 23, 1995

[54] 14,16β-ETHANO-15β, 16(1)-CYCLO-14β-ESTRA-1,3,5(10)-TRIENES

[75] Inventors: James R. Bull, Waterkloof Ridge, South Africa; Walter Elger, Berlin, Germany; Krzysztof Chwalisz, Berlin, Germany; Karl-Heinrich Fritzemeier, Berlin, Germany

[73] Assignee: Schering Aktiengesellschaft, Berlin and Bergkamen, Germany

[21] Appl. No.: 90,220

[22] PCT Filed: Jan. 24, 1992

[86] PCT No.: PCT/EP92/00160
§ 371 Date: Nov. 15, 1993
§ 102(e) Date: Nov. 15, 1993

[87] PCT Pub. No.: WO92/12990
PCT Pub. Date: Aug. 6, 1992

[30] Foreign Application Priority Data

Jan. 24, 1991 [DE] Germany ............... 41 02 244.0

[51] Int. Cl.⁶ .............................................. C07J 53/00
[52] U.S. Cl. ................................... 514/182; 552/510
[58] Field of Search ...................... 552/510; 514/182

[56] References Cited

U.S. PATENT DOCUMENTS

| 4,220,775 | 9/1980 | Rasmusson et al. | 546/77 |
| 4,231,946 | 11/1980 | Ponsold et al. | 260/397.4 |
| 4,542,024 | 9/1985 | Nickisch et al. | 514/178 |
| 4,587,235 | 5/1986 | Bittler et al. | 514/178 |

FOREIGN PATENT DOCUMENTS 0372665  6/1990  European Pat. Off. .

OTHER PUBLICATIONS

Bull et al., "Cycloaddition Route to 14,17-Ethano-and 14-Alkyl-19-norsteroids", *Journal of The Chemical Society. Perkin Transactions 1.*, No. 2 (Feb. 1990), pp. 241–251.

*Primary Examiner*—James H. Reamer
*Assistant Examiner*—Kimberly J. Kestler
*Attorney, Agent, or Firm*—Millen, White, Zelano, & Branigan

[57] ABSTRACT

14,16β-Ethano-15β,16¹-cyclo-14β-estra-1,3,5(10)-trienes of general formula I

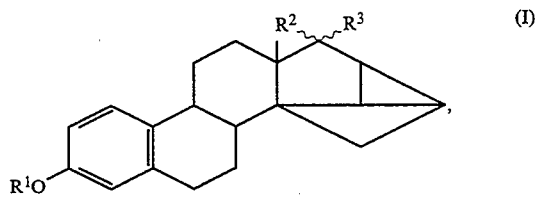

in which
$R^1$ means a hydrogen atom, a $C_1$ to $C_9$ alkyl or $C_1$ to $C_9$ acyl radical,
$R^2$ means a hydrogen atom, a $C_1$ to $C_9$ alkyl radical, a $C_2$ to $C_9$ alkenyl or alkinyl radical and
$R^3$ means a hydroxy group or a $C_1$ to $C_9$ acyloxy radical, as well as a process for their production are described. The new compounds have high (peroral) effectiveness and are suitable for the production of pharmaceutical agents.

4 Claims, No Drawings

14,16β-ETHANO-15β, 16(1)-CYCLO-14β-ESTRA-1,3,5(10)-TRIENES

This invention relates to 14,16β-ethano-15β,16¹-cyclo-14β-estra-1,3,5(10)-trienes of general formula I

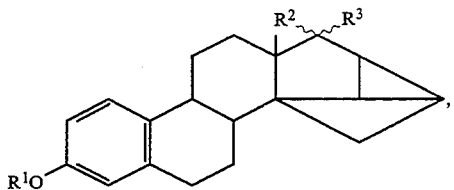

in which
- R¹ means a hydrogen atom, a C₁ to C₉ alkyl or C₁ to C₉ acyl radical,
- R² means a hydrogen atom, a C₁ to C₉ alkyl radical, a C₂ to C₉ alkenyl or alkinyl radical and
- R³ means a hydroxy group or a C₁ to C₉ acyloxy radical, a process for their production, pharmaceutical preparations which contain these compounds as well as their use for the production of pharmaceutical agents.

R² can be present both in 17α-position and in 17β-position and consequently R³ can be present in 17β-position or 17α-position.

As acyl radical R¹ and for the acyl radical in acyloxy radical R³, radicals of organic carboxylic acids with 1–12 carbon atoms are suitable. They are derived from aliphatic, cycloaliphatic, aliphatic-cycloaliphatic, cycloaliphatic-aliphatic and aromatic monocarboxylic acids with 1 to 12 carbon atoms. The number of carbon atoms in the ring varies from 3 to 7. For radicals R¹, R², R³, and the acyl groups of acetic, propionic, butyric, isobutyric, pivalic, caproic, acrylic, crotonic, heptanoic, caprylic, pelargonic, decanoic, undecanoic, dodecanoic, 3-cyclopentylpropionic and benzoic acid are preferred.

In particular, acyl radicals R¹, R² and acyloxy radical R³ are to be derived from those carboxylic acids which have 2 to 8 carbon atoms.

Acyl groups R¹, R² and R³ can also come from dicarboxylic acids with up to 6 carbon atoms; here, in particular, succinic acid is meant.

If R¹ is an alkyl radical, above all the methyl radical is meant; also, ethyl, propyl and isopropyl radicals are of special importance.

As a cycloalkyl radical, the cyclopentyl radical is preferred for R¹.

Within the scope of this invention, the following compounds are to be emphasized:

(16¹S)-14,16β-Ethano-15β,16¹-cyclo-14β-estra-1,3,5(10)-triene-3,17β-diol,
(16¹S)-14,16β-ethano-15β,16¹-cyclo-14β-estra-1,3,5(10)-triene-3,17α-diol,
(16¹S)-17β-(acetyloxy)-14,16β-ethano-15β,16¹-cyclo-14β-estra-1,3,5(10)-trien-3-ol,
(16¹S )-17β-(benzoyloxy)-14,16β-ethano-15β,16¹-cyclo-14β-estra-1,3,5(10)-trien-3-ol,
(16¹S)-17α-(acetyloxy)-14,16β-ethano-15β,16¹-cyclo-14β-estra-1,3,5,(10)-trien-3-ol,
(16¹S)-17α-(benzoyloxy)-14,16β-ethano-15β,16¹-cyclo-14β-estra-1,3,5(10)-trien-3-ol.

The compounds of general formula I according to the invention exhibit a great affinity to the estrogen receptor and they have high estrogenic activity also after peroral administration.

As compounds with high estrogenic activity, for example, the natural estrogens estradiol and estriol (E. Schröder, C. Rufer and R. Schmiechen, Pharmazeutische Chemie [Pharmaceutical Chemistry], 1982, Georg Thieme Verlag, Stuttgart-New York, p. 568 ff) are known. But they are not metabolically stable and, after oral administration, are broken down by oxidation of the 17-hydroxy group to the corresponding, less effective estrone derivative.

By introducing, for example, an ethinyl group on the 17-C atom (ethinylestradiol, loc. cit., p. 574), the oxidation of the 17-hydroxy group can be prevented and the corresponding derivatives consequently have at their disposal high estrogenic activity after peroral administration, Only recently has it been possible to obtain estrogen compounds with high peroral activity not by variations of the substituents in the steroid skeleton but by modification of the steroid skeleton itself. Thus, the bridging of the 14- and 17-carbon atoms of the estradiol with an etheno or ethano bridge blocks the oxidation of the 17β-hydroxy group (J. Chem. Commun., 1986, 451–453 or international patent application PCT/DE87/00361).

Obviously, the oxidation of the 17-hydroxy group is also impeded in the compounds according to the invention by the double bridging (despite the presence of a hydrogen atom on the 17-C atom).

The estrogenic activity of the compounds according to the invention is documented by the results of the estrogen receptor-binding test. In this known in vitro test, tissue from rat uteri is prepared and radioactively labeled ³H-estradiol is used as a reference substance. The compounds, according to the invention (16¹S)-14,16β-ethano-15β,16¹-cyclo-14β-estra-1,3,5(10)-triene-3,17β-diol (A) and (16¹S)-14,16β-ethano-15β,16¹-cyclo-14β-estra-1,3,5(10)-triene-3,17α-diol (B) accordingly have the following competition factors:

(A): $K_A = 2.5$ (B): $K_B = 6.5$.

The invention thus also relates to the use of the compounds of general formula I for the production of pharmaceutical agents.

The compounds according to the invention can be formulated and used in the same way as ethinylestradiol, which is the most-used estrogen. They are processed to the usual pharmaceutical agent forms with the additives, vehicles and/or flavoring substances usual in galenic pharmaceutics according to methods known in the art. For oral administration, in particular tablets, coated tablets, capsules, pills, suspensions or solutions are suitable. For parenteral administration, in particular oily solutions, such as, for example, sesame oil or castor oil solutions, are suitable, which optionally can contain in addition a diluting agent, such as, for example, benzyl benzoate or benzyl alcohol.

The active ingredient concentration in the pharmaceutical compositions depends on the form of administration and the field of use. Thus, for example, capsules or tablets for treating estrogen deficiency symptoms can contain 0.001 to 0.05 mg of active ingredient, oily solutions for intramuscular injection per 1 ml can contain about 0.01 to 0.1 mg of active ingredient and vaginal ointments about 0.1 to 10 mg per 100 ml of ointment. For contraception in the woman, the estrogens according to the invention can be used in combination with gestagens. Tablets or coated tablets for daily intake of a tablet or a coated tablet preferably are to contain 0.003 to 0.05 mg of the estrogen according to the invention and 0.05 to 0.5 mg of a gestagen.

The compounds according to the invention can be used in the case of estrogen deficiency symptoms of the woman, such as, for example, amenorrhea, dysmenorrhea, sterility, endometritis, colpitis and menopausal symptoms and for prevention of osteoporosis. Further, the compounds can be used as estrogen components in hormonal contraceptives (single-phase and multiphase and multistage preparations). Further, they are suitable in connection with other active ingredients for use in active ingredient vehicles implantable in hormone-carrying intrauterine pessaries as well as in transdermal administration systems. The new compounds of general formula I

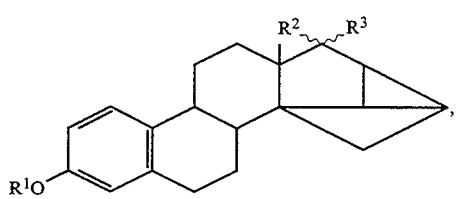
(I)

in which
  $R^1$ means a hydrogen atom, a $C_1$ to $C_9$ alkyl or $C_1$ to $C_9$ acyl radical,
  $R^2$ means a hydrogen atom, a $C_1$ to $C_9$ alkyl radical, a $C_2$ to $C_9$ alkenyl or alkinyl radical and
  $R^3$ means a hydroxy group or a $C_1$ to $C_9$ acyloxy radical, are produced by either a compound of general formula II

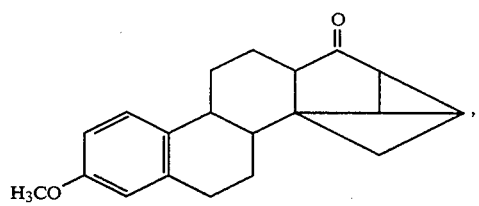
(II)

being reduced with a complex hydride to a compound of general formula Ia

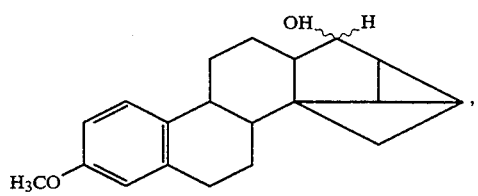
(Ia)

optionally the C-17 isomers being separated, optionally the 3-alkyl ether being cleaved while obtaining the compounds of formula Ib

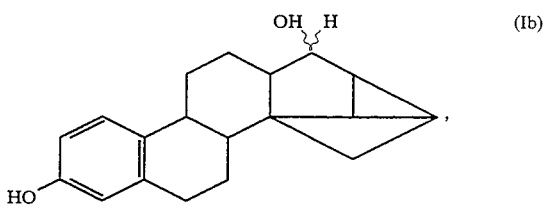
(Ib)

or in the compound of general formula II the 3-alkyl ether optionally being cleaved and the obtained compound of formula III

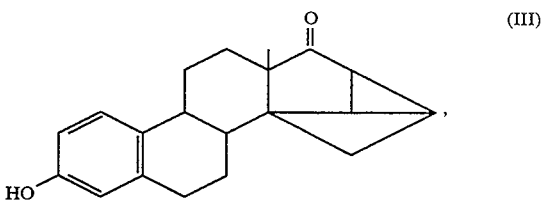
(III)

being reacted with a compound of general formula IV

R—X (IV), in which R stands for a $C_1$ to $C_9$ alkyl radical or a $C_2$ to $C_9$ alkenyl or alkinyl radical and X stands for an Li, Na or K atom, to a compound of general formula Ic

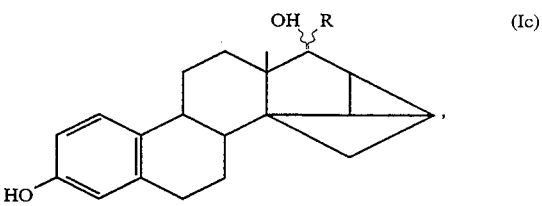
(Ic)

in which R has the above-indicated meaning and optionally the C-17 alcohols of formulas Ia, Ib or Ic being partially, totally or successively esterified by reaction with a corresponding $C_1$ to $C_9$ carboxylic acid chloride or anhydride.

As typical representatives for the complex hydride to be used for reduction of the compound of general formula II, for example, lithium aluminum hydride or sodium borohydride can be mentioned. In the case of the reduction, the C-17 alcohols result as a mixture of the α,β-isomers, which are (can be) separated by fractional crystallization or chromatography.

The cleavage of the 3-alkyl ethers of general formula Ia is possible with diisobutylaluminum hydride in an inert solvent, such as, for example, toluene, under elevated temperature (i.a., with refluxing). The cleavage of the alkyl group in the 3-alkyl ethers of general formula II takes place under the same conditions. A Lewis acid, such as, for example, trimethylsilyl iodide, can also be used for ether cleavage in a polar solvent, such as acetonitrile.

The introduction of a $C_1$ to $C_9$ alkyl, a $C_2$ to $C_9$ alkenyl or alkinyl side chain in 17-position of the compound of formula III is possible by nucleophilic addition of a corresponding alkali alkyl, alkali alkenyl or alkali alkinyl compound (alkali=lithium, sodium, potassium) to the 17-keto group according to the standard processes. Also, in general, both C-17 isomers, which can be separated by chromatography or other usual processes, can be obtained here.

Finally, the alcohols of formulas Ia, Ib or Ic can be esterified according to usual processes, e.g., by reaction with the corresponding carboxylic acid chloride or anhydride (depending on the finally desired $R^1$, $R^2/R^3$) in the presence of a base such as 4-dimethylaminopyridine. By keeping in mind the different reactivities of the two free hydroxy groups in the compounds of formula Ib or Ic as well as by the amount of esterification reagent used, the partial, total or successive esterification of the initial compounds can be achieved. If $R^1$ is to be a hydrogen atom, the 3-acyloxy group can again be selectively saponified after complete esterification of Ib or Ic.

The production of the initial compound of general formula II (see diagram below) starts from the known dienol acetate 1, which is reacted in a Diels-Alder cycloaddition with chloroacrylonitrile. The reaction is preferably performed under elevated pressure (2-20 bars) in an inert, organic solvent, such as benzene, toluene, dichloromethane at temperature between 50°-120° C. The treatment of cycloadduct 2 with strong bases such as alkali metal hydroxides, lithium diisopropylamide, sodium amide produces ketonitrile 4, ketalization to 6, reduction of 6 with diisobutylaluminum hydride to aldehyde 7, rhodium-catalyzed decarbonylation of 7 to 8 and deketalization produces central initial product 9.

This invention also extends to the initial compounds of general formula II (=9).

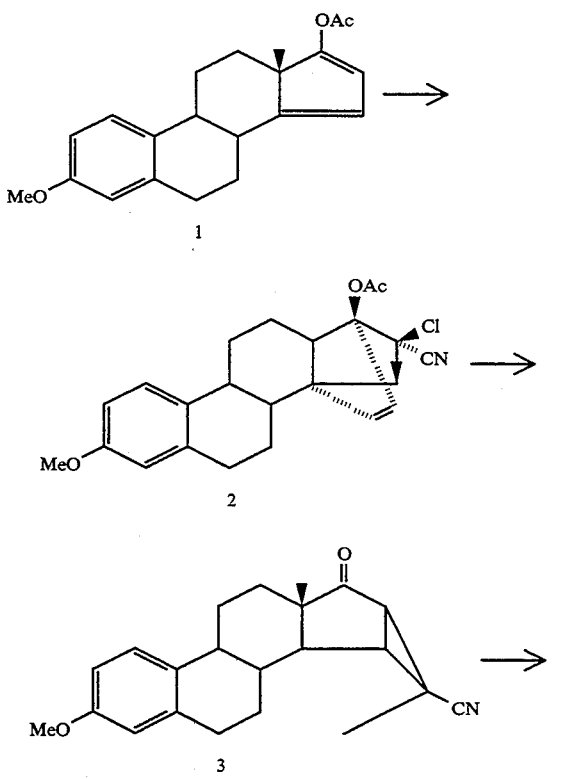

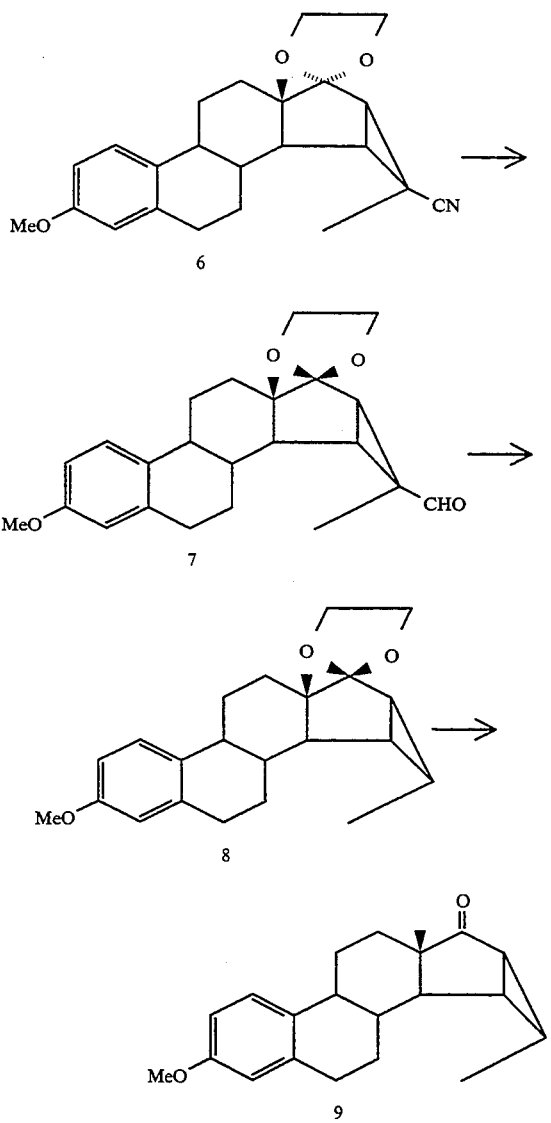

The following examples are used to explain the invention in more detail:

Production of initial compound (9)

16β-Chloro-16α-cyano-3-methoxy-14,17α-ethenoestra-1,3,5(10)-trien-17β-yl-acetate (2)

A mixture of 3-methoxyestra-1,3,5(10),14,16-pentaen-17-yl-acetate (1) (2 g; 6.2 mmol) and 1-chloro-1-cyano-ethylene (1 ml; 12.6 mmol) in benzene (7 ml) is kept in a closed glass pressure pipe with stirring at 80° C. After 7 days, the reaction mixture is filtered on Celite and concentrated by evaporation under reduced pressure. Crystallization of the residue from chloroform-methanol produces pure cycloadduct (2) (1.67 g; 66%).

Melting point: 182°-185° C. $[\alpha]_D+130°$ (c 0.6) $C_{24}H_{26}ClNO_3$ Found: C 70.1 H 6.6 N 3.4% M+ 412 Calculated: C 70.0 H 6.4 N 3.4% M 412 Chromatography of the mother liquor produces even more cycloadduct (2) (400 mg; 16%)

Alkaline treatment of the cycloadduct a) Aqueous 2M potassium hydroxide solution (1.1 ml; 2.2 mmol) is added with stirring to a solution of cycloadduct (2) (360 mg; 0.87 mmol) in tetrahydrofuran (7.2 ml) and dimethyl sulfoxide (7.2 ml) under nitrogen at 0° C. After 3 hours, saturated aqueous ammonium chloride solution is added and the mixture is extracted with chloroform. The extract is washed with common salt solution and water, dried (MgSO$_4$) and concentrated by evaporation under reduced pressure. Recrystallization of the crude product from chloroform/methanol produces (16$^1$R)-3-methoxy-17-oxo-14,16$\beta$-ethano-15$\beta$,16$^1$-cyclo-14$\beta$-estra-1,3,5(10)-triene-16$^1$-carbonitrile (4) (262 mg; 90%).

Melting point: 158°–161° C. (from chloroform-methanol) [$\alpha$]$_D$+137° C. (c 0.8) C$_{22}$H$_{23}$NO$_2$ Found: C 79.2 H 7.0 N 4.1% M+ 333 Calculated: C 79.3 H 7.0 N 4.2% M 333 Chromatography of the mother liquor on silica gel (3.8 g) with ethyl acetate/hexane (1:3) as eluant produces additional (4).

b) Aqueous 1.5M potassium hydroxide solution (10 ml; 15.0 mmol) is added with stirring to a solution of cycloadduct (2) (1 g; 2.43 mmol) at 25° C. under nitrogen. After 23 hours, ammonium chloride solution is added and the mixture is extracted with chloroform. The extract is washed with common salt solution, dried (MgSO$_4$) and concentrated by evaporation under reduced pressure, and (16$^1$R)-3-methoxy-17-oxo-14,16$\beta$-ethano-15$\beta$,16$^1$-cyclo-14$\beta$-estra-1,3,5(10)-triene-16$^1$-carboxamide (5) (684 mg; 80%) is obtained;

Melting point: 252°–255° C. (from ethanol) [$\alpha$]$_D$+96° C. (c 0.9) C$_{22}$H$_{25}$NO$_3$ Found: C 75.3 H 6.9 N 3.8% M+ 351 Calculated: C 75.2 H 7.2 N 4.0% M 351

(16$^1$R) 17,17-Ethylenedioxy-3-methoxy-14,16$\beta$-ethano-15$\beta$,16$^1$-cyclo-14$\beta$-estra-1,3,5(10)-triene-16$^1$-carbonitrile (6)

A mixture of carbonitrile (4) (540 mg; 1.6 mmol), ethylene glycol (2.0 ml) and para-toluenesulfonic acid (50 mg; 0.29 mmol) in toluene (54 ml) is slowly distilled in a Dean-and-Stark apparatus. After 7.5 hours, after the volume has decreased to about 30 ml, the mixture is refluxed for another 17 hours by recycling the condensate through molecular sieve (4A). Aqueous sodium bicarbonate solution is added and the mixture is extracted with toluene. The extract is washed with water and sodium bicarbonate solution, dried (MgSO4) and concentrated by evaporation under reduced pressure. The crystalline residue (632 mg) is recrystallized from chloroform/methanol, and ketal (6) (565 mg; 92%) is obtained.

Melting point: 232°–237° C.; [$\alpha$]$_D$+122° (C 1.0) C$_{24}$H$_{27}$NO$_3$ Found: C 76.1 H 7.3 N 3.7% M+ 377 Calculated: C 76.4 H 7.2 N 3.7% M 377

Flash chromatography of the mother liquor on silica gel (7 g) with ethyl acetate-toluene (1:19) as eluant produces additional ketal (6) (39 mg; 6%)

(16$^1$R)-17,17-Ethylenedioxy-3-methoxy-17-oxo-14,16$\beta$-ethano-15$\beta$,16$^1$-cyclo-14$\beta$-estra-1,3,5(10)-triene-16$^1$-carbaldehyde (7)

A solution of ketal (6) (400 mg; 1.06 mmol) in anhydrous toluene (80 ml) is treated at −78° C. under nitrogen with diisobutylaluminum hydride (20% in hexane, 3.6 ml). After 160 minutes, aqueous ammonium chloride solution is added. The aqueous phase is acidified with dilute sulfuric acid and extracted with ethyl acetate, washed with aqueous sodium bicarbonate solution and water, dried (MgSO$_4$) and evaporated to dryness under reduced pressure. Flash chromatography on silica gel (40g) with ethyl acetate/toluene (1:9) as eluant yields 16$^1$-carbaldehyde (7) (335 mg; 83%).

Melting point: 190°–194° C. (from chloroform-hexane) [$\alpha$]$_D$+148° (C 1.0) C$_{24}$H$_{28}$O$_4$ Found: C 75.7 H 7.2% M+ 380 Calculated: C 75.8 H 7.4% M 380

(16$^1$S)-17,17-Ethylenedioxy-3-methoxy-14,16$\beta$-ethano-15$\beta$,16$^1$-cyclo-14$\beta$-estra-1,3,5(10)-triene (8)

A solution of 16$^1$-carbaldehyde (7) (340 mg; 0.89 mmol) and RhCl(PPh$_3$)$_3$ (912 mg; 0.99 mmol) in degassed toluene (25 ml) is refluxed under nitrogen for 20 hours. After adding ethanol, most of the formed RhCl(CO)(PPh$_3$)$_2$ is removed by filtration. The filtrate is evaporated to dryness. Chromatography of the raw material (805 mg) on silica gel (34 g) with ethyl acetate/toluene (1:99) as eluant yields product (8) (291 mg; 92%). Melting point: 159°–163° C. (from chloroform-methanol); [$\alpha$]$_D$+117° (C 1.0) C$_{23}$H$_{28}$O$_3$ Found: C 78.4 H 8.2% M+ 352 Calculated: C 78.4 H 8.0% M 352

(16$^1$S)-3-Methoxy-14,16$\beta$-ethano-15$\beta$,16$^1$-cyclo-14$\beta$-estra-1,3,5(10)-trien-17-one (9)

A solution of (8) (150 mg; 0.43mmol) in tetrahydrofuran (6 ml) and methanol (18ml) is treated with 6M hydrochloric acid (1.2 ml; 7.2mmol) at 0° C. After 6 minutes, solid sodium bicarbonate is added, the mixture is diluted with water and extracted with chloroform. The extract is washed with aqueous sodium bicarbonate solution and water, dried (MgSO4) and concentrated by evaporation under reduced pressure. Crystallization of the residue (154 mg) from chloroform/methanol produces 17-ketone (9) (110 mg; 84%).

Melting point: 179°–184° C. [$\alpha$]$_D$+171° (c 1.0) C$_{21}$H$_{24}$O$_2$ Found: C 81.7 H 7.7% M+ 308 Calculated: C 81.8 H 7.8% M 308

Chromatography of the residual mother liquor on silica gel (1.6 g) with ethyl acetate as eluant yields additional (9) (10 mg; 8%).

EXAMPLE 1

(16$^1$S)-3-Methoxy-14,16$\beta$-ethano-15$\beta$,16$^1$-cyclo-14$\beta$-estra-1,3,5(10)-trien-17$\beta$-ol (10) and

EXAMPLE 2

(16$^1$S)-3-Methoxy-14,16$\beta$-ethano-15$\beta$,16$^1$-cyclo-14$\beta$-estra-1,3,5(10)-trien-17$\alpha$-ol (11)

a) Lithium aluminum hydride is added in portions with stirring to a solution of (9) (398 mg; 1.3 mmol) in tetrahydrofuran (24 ml) under nitrogen and the mixture is refluxed for 27 hours, cooled and excess reagent is decomposed by adding aqueous ammonium chloride solution. The mixture is extracted with ethyl acetate, the extract is washed with aqueous ammonium chloride solution and water, dried (MgSO$_4$) and concentrated by evaporation under reduced pressure. Chromatography of the residue (411 mg) on silica gel (40 g) with ethyl acetate/chloroform (1:99) as eluant yields 17$\beta$-alcohol (10) (116 mg; 30%).

Melting point: 141°–145° C. (from methanol/water) [$\alpha$]$_D$+133° (c 0.55) C$_{21}$H$_{25}$O$_2$Found: C 81.0 H 8.5% M+ 310 Calculated: C 81.3 H 8.4% M 310 and 17$\alpha$-alcohol (11) (169 mg; 42%)

Melting point: 129°–132° C. (from ethyl acetate/hexane) [$\alpha$]$_D$+75° (C 0.52) C$_{21}$H$_{26}$O$_2$ Found: C 81.3 H 8.3% M+ 310 Calculated: C 81.3 H 8.4% M 310 b) Diisobutylaluminum hydride (20% solution in hexane; 2.7 ml) is added with stirring to a solution of (4) (290 mg; 0.87 mmol) in toluene (50 ml) under nitrogen at −78° C. The reaction is terminated after 60 minutes with aqueous ammonium chloride solution. Then, ethyl acetate and then water are added. The mixture is acidified and extracted with ethyl acetate, the extract is washed with aqueous sodium bicarbonate solution and water, dried (MgSO$_4$) and concentrated by evaporation under reduced pressure to product (12+13) (306 mg), which is used directly for the next reaction step. The mixture of 17-hydroxy-16$^1$-carbaldehyde (12+13) (306 mg) and RhCl(PPh$_3$)$_3$ (700 mg; 0.76 mmol) in degassed toluene (42 ml) is refluxed for 19 hours under nitrogen. Ethanol is added to the cooled solution, and the mixture is filtered. The filtrate is concentrated by evaporation under reduced pressure and the residue is chromatographed on silica gel (62 g) with ethyl acetate/chloroform (1:99), and first 17β-alcohol (10) (97 mg) and subsequently 17α-alcohol (11) (116 mg) are obtained.

EXAMPLE 3

(16$^1$S)-14,16β-Ethano-15β,16$^1$-cyclo-14β-estra-1,3,5(10)-triene-3,17β-diol (14)

Diisobutylaluminum hydride (20% solution in hexane; 3.9 ml) is added with stirring to a solution of (10) (150 mg; 0.47 mmol) in toluene (27 ml) under nitrogen, the mixture is refluxed for 23.5 hours, cooled to room temperature and the reaction is terminated by the addition of aqueous ammonium chloride solution. Then, ethyl acetate and then water are added. The mixture is acidified with hydrochloric acid and extracted with ethyl acetate. The extract is washed with aqueous ammonium chloride solution and water, dried (MgSO$_4$) and concentrated by evaporation under reduced pressure while obtaining a product (150 mg) which is chromatographed under pressure on silica gel (15 g) with methanol/chloroform (1:19) as eluant while obtaining (16$^1$S)-14,16β-ethano-15β,16$^1$-cyclo-14β-estra-1,3,5(10)-triene-3,17β-diol (14) (113 mg; 79%).

Melting point: 247°–249° C. (from chloroform/methanol) [α]$_D$+118° (C 0.41) C$_{20}$H$_{24}$O$_2$ Found: C 81.0 H 7.8% M+ 296 Calculated: C 81.0 H 8.2% M 296

EXAMPLE 4

(16$^1$S)-14,16β-Ethano-15β,16$^1$-cyclo-14β-estra-1,3,5(10)-triene-3,17α-diol (15)

Analogous treatment of 17α-alcohol (11) (109 mg; 0.35 mmol) with diisobutylaluminum hydride, subsequent chromatography of the product on silica gel (12 g) with ethyl acetate/chloroform (1:1) as eluant produces (16$^1$S)-14,16β-ethano-15β,16$^1$-cyclo-14β-estra-1,3,5(10)-triene-3,17α-diol (15) (100 mg; 95%).

Melting point: 205°–210° C. (from acetone/hexane) [α]$_D$+79 (c 0.46 in tetrahydrofuran) C$_{20}$H$_{24}$O$_2$ Found: C 80.9 H 7.9% M+ 296 Calculated: C 81.0 H 8.2% M 296

EXAMPLE 5

(16$^1$S)-17β-(Acetyloxy)-14,16β-ethano-15β,16$^1$-cyclo-14β-estra-1,3,5(10)-trien-3-ol (18)

a) (161$^1$S)-3-[[Dimethyl(1,1-dimethylethyl)silyl]oxy]-14,16β-ethano-15β,16$^1$-cyclo-14β-estra-1,3,5(10)-trien-17β-ol (16)

241 mg of (16$^1$S)-14,16β-ethano-15β,16$^1$-cyclo-14β-estra-1,3,5(10)-triene-3,17β-diol (14) is dissolved in 3 ml of absolute dimethylformamide. 173 mg of imidazole and 184 mg of dimethyl-(1,1-dimethylethyl)silyl chloride are added and allowed to stir for 1.5 more hours at room temperature. Then, the reaction solution is poured on ice water. It is extracted with ethyl acetate, the organic phase is washed with saturated sodium chloride solution, dried on sodium sulfate, filtered and concentrated by evaporation in a vacuum. The crude product is chromatographed on silica gel with a mixture of hexane/ethyl acetate. 251 mg of (16) is obtained as white foam.

$^1$H-NMR (CDCl$^3$): δ=7.03 dbr (J=9 Hz,1H,H-1); 6.53 dd (J=9, 2.5 Hz,1H,H-2); 6.47 dbr (J=2.5 Hz,1H,H-4); 3.88 m (1H,H-17); 0.87 s (9H,t-Bu); 0.75 s (3H,C-18); 0.08 s (6H,SiMe$_2$)

b) (16$^1$S)-17β-(Acetyloxy)-3-[[dimethyl(1,1-dimethylethyl)silyl]oxy]-14,16β-ethano-15β,16$^1$-cyclo-14β-estra-1,3,5(10)-triene (17)

100 mg of the compound described under a) is dissolved in 2.5 ml of absolute dichloromethane. 0.05 ml of triethylamine, a spatula tip full of 4-dimethylaminopyridine as well as 0.035 ml of acetic anhydride are added and allowed to stir for 1 more hour at room temperature. Then, the reaction solution is mixed with water. It is stirred for 30 more minutes and then extracted with ethyl acetate. The organic phase is washed with 2 n aqueous hydrochloric acid, saturated sodium bicarbonate solution as well as saturated sodium chloride solution, dried on sodium sulfate, filtered and concentrated by evaporation in a vacuum. 104 mg of (17), which is used without purification in the next step, is obtained.

c) (16$^1$S)-17$^{62}$-(Acetyloxy)-14,16β-ethano-15β,16$^1$-cyclo-14β-estra-1,3,5(10)-trien-3-ol (18)

104 mg of the compound described under b) is dissolved in 1 ml of absolute tetrahydrofuran. It is mixed with 182 mg of tetrabutylammonium fluoride trihydrate and allowed to stir for 30 more minutes at room temperature. Then, the reaction solution is poured on ice-cold saturated sodium bicarbonate solution. It is extracted with ethyl acetate, the organic phase is washed with saturated sodium chloride solution, dried on sodium sulfate, filtered and concentrated by evaporation in a vacuum. The crude product is recrystallized from diisopropyl ether. 45 mg of (18) is obtained as white crystals.

Melting point=231.8° C. [α]$^{20}_D$=+145.3° (CHCl$_3$; c=0.505)

EXAMPLE 6

(16$^1$S)-17β-(Benzoyloxy)-14,16β-ethano-15β,16$^1$-cyclo-14β-estra-1,3,5(10)-trien-3-ol (20)

a) (16$^1$S)-3-[[Dimethyl(1,1-dimethylethyl)silyl]oxy]-17β-(benzoyloxy)-14,16β-ethano-15β,16$^1$-cyclo-14β-estra-1,3,5(10)-triene (19)

100 mg of the compound described under example 5a) is dissolved in 0.65 ml of absolute pyridine. 0.07 ml of benzoyl chloride is added and allowed to stir for 1.5 more hours at room temperature. Then, the reaction solution is poured on water. It is extracted with ethyl acetate, the organic phase is washed twice with saturated sodium bicarbonate solution and once with saturated sodium chloride solution, dried on sodium sulfate, filtered and concentrated by evaporation in a vacuum. The crude product is chromatographed on silica gel with a mixture of hexane/ethyl acetate. 100 mg of (19) is obtained as white foam.

b) (16$^1$S)-17β-(Benzoyloxy)-14,16β-ethano-15β,16$^1$-cyclo-14β-estra-1,3,5(10)-trien-3-ol (20)

Analogously to example 5c), 100 mg of the compound, produced under a), in 1 ml of tetrahydrofuran is reacted with 154 mg of tetrabutylammonium fluoride trihydrate. The crude product is recrystallized from diisopropyl ether. 61 mg of (20) is obtained as white crystals.

Melting point=186° C. [α]$^{20}_D$=+145.8° (CHCl$_3$; c=0.510)

EXAMPLE 7

(16¹S)-17α-(Acetyloxy)-14,16β-ethano-15β,16¹-cyclo-14β-estra-1,3,5(10)-trien-3-ol (23)

a) (16¹S)-3-[[Dimethyl(1,1-dimethylethyl)silyl]oxy]-14,16β-ethano-15β,16¹-cyclo-14β-estra-1,3,5(10)-trien-17α-ol (21)

Analogously to example 5a), 384 mg of (16¹S)-14,16β-ethano-15β,16¹-cyclo-14β-estra-1,3,5(10)-triene-3,17α-diol (15), 275 mg of imidazole and 250 mg of dimethyl-(1,1-dimethylethyl)silyl chloride in 5 ml of absolute dimethylformamide are reacted After column chromatography, 380 mg of (21) is obtained as white foam.

$^1$H-NMR (CDCl$_3$): δ7.14 dbr (J=9 Hz,1H,H-1); 6.62 dd (J=9, 2.5 Hz,1H,H-2); 6.55 dbr (J=2.5 Hz,1H,H-4); 4.18 m (1H,H-17); 0.97 s (9H,t-Bu); 0.90 s (3H,C-18); 0.10 s (6H,SiMe$_2$)

b) (16¹S)-17α-(Acetyloxy)-3-[[dimethyl(1,1-dimethylethyl)silyl]oxy]-14,16β-ethano-15β,16¹-cyclo-14β-estra-1,3,5(10)-triene (22)

Analogously to example 5b), 100 mg of the compound, produced under a), is reacted with 0.05 ml of triethylamine, 0.04 ml of acetic anhydride as well as a spatula tip full of 4 dimethylaminopyridine in 2 ml of methylene chloride. 90 mg of (22), which is used as crude product in the next step, is obtained.

c) (16¹S)-17α-(Acetyloxy)-14,16β-ethano-15β,16¹-cyclo-14β-estra-1,3,5(10)-trien-3-ol (23)

Analogously to example 5c), 90 mg of the compound produced under b) and 160 mg of tetrabutylammonium fluoride trihydrate are reacted in 1 ml of tetrahydrofuran. The crude product is recrystallized from diisopropyl ether. 50 mg of 23) is obtained as white crystals. Melting point=189.5° C. [α]$^{20}_D$=+94.3° (CHCl$_{13}$; c=0.510)

EXAMPLE 8

(16¹S)-17α-(Benzoyloxy)-14,16β-ethano-15β,16¹-cyclo-14β-estra-1,3,5(10)-trien-3-ol (25)

a) (16¹S)-3-[[Dimethyl(1,1-dimethylethyl)silyl]oxy]-17α-(benzoyloxy)-14,16β-ethano-15β,16¹-cyclo-14β-estra-1,3,5(10)-triene (24)

Analogously to example 6a), 100 mg of the compound produced under example 7a) and 0.07 ml of benzoyl chloride are reacted in 0.6 ml of absolute pyridine. After chromatography, 95 mg of (24) is obtained as white foam.

b) (16¹S)-17α-(Benzoyloxy)-14,16β-ethano-15β,16¹-cyclo-14β-estra-1,3,5(10)-trien-3-ol (25)

Analogously to example 5c), 95 mg of the compound produced under a) and 150 mg of tetrabutylammonium fluoride trihydrate are reacted in 1.5 ml of absolute tetrahydrofuran. The crude product is recrystallized from diisopropyl ether. 53 mg of 25) is obtained as white crystals Melting point=170.0° C. [α]$^{20}_D$=+18.4° (CHCl$_3$; c=0.505)

We claim:

1. 14,16β-Ethano-15β,16¹-cyclo-14β-estra-1,3,5(10)-trienes of general formula I

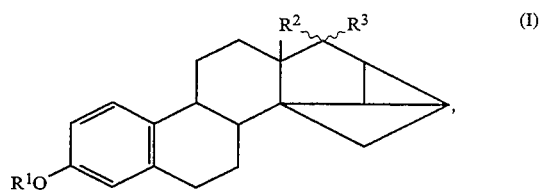

in which

R$^1$ is a hydrogen atom, a C$_1$ to C$_9$ alkyl or C$_1$ to C$_9$ acyl radical, R$^2$ is a hydrogen atom, a C$_1$ to C$_9$ alkyl radical, a C$_2$ to C$_9$ alkenyl or alkinyl radical and R$^3$ is a hydroxy group or a C$_1$ to C$_9$ acyloxy radical.

2. A compound of claim 1 selected from the group consisting of (16¹S)-14,16β-Ethano-15β,16¹-cyclo-14β-estra-1,3,5(10)-triene-3,17β-diol and (16¹S)-14,16β-ethano-15β,16¹-cyclo-14β-estra-1,3,5(10)-triene-3,17α-diol.

3. A compound of general formula II

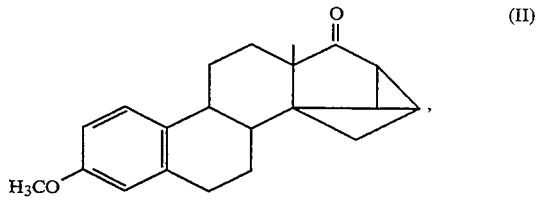

4. A pharmaceutical preparation, comprising one or more compound(s) of claim 1 and a pharmaceutically compatible vehicle.

* * * * *